US011931250B2

(12) United States Patent
Kamradt

(10) Patent No.: US 11,931,250 B2
(45) Date of Patent: Mar. 19, 2024

(54) VOICE PROSTHESIS WITH CONNECTING FEATURE

(71) Applicant: Brian Kamradt, Indianapolis, IN (US)

(72) Inventor: Brian Kamradt, Indianapolis, IN (US)

(73) Assignee: Eon Meditech Pvt. Ltd., Gujarat (IN)

( * ) Notice: Subject to any disclaimer, the term of this patent is extended or adjusted under 35 U.S.C. 154(b) by 637 days.

(21) Appl. No.: 17/052,733

(22) PCT Filed: May 3, 2019

(86) PCT No.: PCT/US2019/030752
§ 371 (c)(1),
(2) Date: Nov. 3, 2020

(87) PCT Pub. No.: WO2019/213629
PCT Pub. Date: Nov. 7, 2019

(65) Prior Publication Data
US 2021/0228339 A1    Jul. 29, 2021

Related U.S. Application Data

(63) Continuation-in-part of application No. 15/932,830, filed on May 3, 2018, now abandoned.

(51) Int. Cl.
*A61F 2/20*    (2006.01)
(52) U.S. Cl.
CPC ...... *A61F 2/203* (2013.01); *A61F 2220/0033* (2013.01)
(58) Field of Classification Search
CPC .................. A61F 2/203; A61F 2220/0033
See application file for complete search history.

(56) References Cited

U.S. PATENT DOCUMENTS

| 4,435,853 | A | | 3/1984 | Blom et al. |
| 4,465,068 | A | | 8/1984 | Cantu |
| 4,820,304 | A | | 4/1989 | Depel et al. |
| 4,911,716 | A | * | 3/1990 | Blom ............... A61F 2/203 |
| | | | | 128/200.26 |

(Continued)

FOREIGN PATENT DOCUMENTS

EP    0551198 B1    3/1998

OTHER PUBLICATIONS

International Search Report, International Searching Authority, PCT/US2019/030752, dated Jul. 17, 2019.

(Continued)

*Primary Examiner* — Suzette J Gherbi
(74) *Attorney, Agent, or Firm* — Reichel Stohry Dean LLP; Mark C. Reichel; Natalie J. Dean

(57) ABSTRACT

A voice prosthesis comprising a outer cannula and an inner cannula wherein the outer cannula is generally in the shape of a spool and comprises two flanges connected by a hollow annular stem therebetween, and the inner cannula comprises a proximal flange and a stem configured to fit within a passageway of the stem of the outer cannula. The outer cannula comprises a retaining slot on its outer proximal edge which can be used to rotationally secure an obround inner cannula proximal flange. The inner cannula may also comprise windows for use with retaining nubs disposed on the interior of the outer cannula passageway and an insertion tool having a moveable protrusions.

20 Claims, 16 Drawing Sheets

(56) References Cited

U.S. PATENT DOCUMENTS

| | | | |
|---|---|---|---|
| 5,123,922 A | 6/1992 | Berg | |
| 5,480,432 A * | 1/1996 | Suding | A61F 2/203 623/9 |
| 5,578,083 A | 11/1996 | Laguette et al. | |
| 5,632,775 A * | 5/1997 | Suding | A61F 2/203 623/9 |
| 5,693,097 A | 12/1997 | Laguette et al. | |
| 6,538,222 B2 | 3/2003 | Hsu | |
| 7,166,128 B1 * | 1/2007 | Persson | A61F 2/203 623/9 |
| 10,314,692 B2 * | 6/2019 | Persson | A61F 2/203 |
| 10,413,399 B2 * | 9/2019 | Blom | A61F 2/20 |
| 10,596,337 B2 * | 3/2020 | Kamradt | A61F 2/203 |
| 11,173,267 B2 * | 11/2021 | Markwardt | A61F 2/203 |
| 11,497,871 B2 * | 11/2022 | Kamradt | A61M 16/1045 |
| 2004/0024455 A1 | 2/2004 | De Vries et al. | |
| 2005/0256573 A1 | 11/2005 | Seder et al. | |
| 2009/0036876 A1 * | 2/2009 | Tran | A61F 2/203 606/1 |
| 2009/0036983 A1 | 2/2009 | Tran | |
| 2009/0043386 A1 | 2/2009 | Persson | |
| 2009/0259310 A1 | 10/2009 | Blom | |
| 2011/0264214 A1 | 10/2011 | Nelson | |
| 2015/0327993 A1 * | 11/2015 | Persson | A61F 2/203 623/9 |
| 2023/0121047 A1 * | 4/2023 | Glen | A61M 16/0468 128/207.16 |

OTHER PUBLICATIONS

Written Opinion of the International Searching Authority, International Searching Authority, PCT/US2019/030752, dated Jul. 17, 2019.

* cited by examiner

VOICE PROSTHESIS WITH CONNECTING FEATURE

PRIORITY AND RELATED APPLICATION

The present patent application is related to, and claims the priority benefit of, U.S. Nonprovisional patent application Ser. No. 15/932,830, filed May 3, 2018, the contents of which are hereby incorporated by reference in their entirety into this disclosure.

TECHNICAL FIELD

The present disclosure relates to a voice prosthesis having an outer cannula and a removable inner cannula and in particular to a voice prosthesis having a disposable inner cannula.

BACKGROUND

When a person's larynx has been removed by surgery due to pathological changes in the throat, the trachea is sutured to an opening in the throat (tracheostoma). By the surgery, the person has lost the ability to speak, and in order to restore this ability to speak a method has been applied for several years, in a voice prosthesis of the kind referred to above is mounted in a fistula, i.e. a passage between trachea and esophagus. At speech, the tracheostoma is occluded by sealing the same either by the patient placing the fingers against the tracheostoma or by the tracheostoma being closed by an in connection therewith provided stoma valve. Then, the expiration air is pressed from the lungs through the voice prosthesis into esophagus where the mucous membranes of the throat are brought into vibration and speech is produced as a consequence thereof. Several voice prostheses are described in U.S. Pat. Nos. 4,911,716, 4,435,853, 4,820,304, and DD-A1-275183. The voice prosthesis is fixed in the fistula by means of two flanges on the spool-shaped element. The spool-shaped element can be cylindrical or oval and preferably it is made of silicon rubber. All existing voice prostheses have in common that they provide a check valve function, which means that the valve mechanism normally is closed but opens when air is pressed from trachea via the valve to esophagus. The valve mechanism is maintained in the closed position by spring bias which in most cases is maintained by elasticity of the material from which the voice prosthesis is made.

When existing voice prostheses are mounted in the fistula the function is acceptable initially but they have a non-acceptably short life due to growth of fungus, candida, will cover the sealing surfaces of the valve mechanism and causing an obstruction of the valve which causes leakage at the intake of beverages and is the primary reason for exchange of the voice prosthesis. Also, the fatigue of the spring bias (the material of the voice prosthesis) so that the valve as a consequence thereof will be partly open in the normal position causing leakage through the voice prosthesis.

The following patents are also of interest: U.S. Pat. Nos. 3,693,624, 4,315,505, 5,314,470, 5,578,083, and 7,166,128. No representation is intended by this listing that a thorough search of material prior art has been conducted, or that no better art than listed is available.

BRIEF SUMMARY

As mentioned above the growth of candida on the sealing surfaces of the voice prosthesis is the main reason for the necessity of exchanging the voice prosthesis. It is an object of the present invention to provide a voice prostheses with outer cannula, which remains in place mounted in the fistula, and a removable, disposable, and inexpensive inner cannula, which serves as an inner lining of the outer cannula and contains said valve mechanism. Thus, to clear the growth of fungus, candida, covering the sealing surfaces of the valve mechanism and causing an obstruction of the valve passage way, the inner cannula can be removed, cleaned, or disposed of and then replaced. An important feature of the inner cannula of the present invention, is its disposability. The inner cannula can be quickly and easily produced in large quantities using an extruded molding process and then end-formed to create the flange at the proximal end using a heating process. Furthermore, dimensional tolerances are held close only in the distal area of the inner cannula to assure an adequate seal with the outer cannula.

Further advantageous features of the invention are defined in the dependent claims.

In another embodiment, the voice prosthesis comprises a an inner cannula comprising a distal end and proximal flange connected by a annular second stem, the stem comprising a passageway therethrough; an outer cannula comprising a distal flange and a proximal flange connected by an annular first stem, the stem comprising a passageway therethough; and the outer cannula comprising a slot configured to secure the inner cannula proximal flange.

In a further embodiment, the voice prosthesis comprises the slot extends along a portion of the outer cannula proximal flange; the inner cannula proximal flange has an obround shape; wherein the inner cannula proximal flange comprises a thickness less than the thickness of the slot.

In another embodiment of the voice prosthesis, the slots are disposed along the outer circumferential edge of the outer cannula proximal end and. The slots comprise two 90 degree arcs located 180 degrees from each other.

An embodiment of the voice prosthesis comprising windows disposed on the inner cannula stem at or near the inner cannula proximal flange and an insertion tool, the insertion comprising protrusions configured to extend through the windows.

In another embodiment of the voice prosthesis, the inner cannula can be rotationally secured to the outer cannula.

In another embodiment a method of deploying a voice prosthesis comprises the steps of: inserting an inner cannula into an outer cannula wherein: the inner cannula comprises a stem and a obround proximal flange; and the outer cannula comprises a passageway configured to accept said stem, and a retaining slot disposed on an outer cannula proximal flange, the retaining slot extending along a portion of the outer cannula proximal flange; wherein the step of inserting an inner cannula into an outer cannula comprises inserting the stem into the passageway.

In another embodiment, the method of deploying a voice prosthesis further comprises the step of rotating the inner cannula such that the obround proximal flange is disposed within the retaining slot.

In another embodiment, the method of deploying a voice prosthesis further comprises attaching an insertion tool to an inner cannula wherein the inner cannula comprises windows the insertion tool comprises moveable protrusions configured to extend through the windows; the step of inserting an inner cannula into an outer cannula and the step of rotating the inner cannula such that the obround proximal flange is disposed within the retaining slot is performed by operating the insertion tool.

The present disclosure includes disclosure of a voice prosthesis device, comprising an inner cannula comprising a distal end and a proximal flange connected by a annular second stem, the annular second stem defining a passageway therethrough; and an outer cannula comprising a distal flange and a proximal flange connected by an annular first stem, the annular first stem defining a passageway therethough; wherein the inner cannula comprises a valve; and wherein the outer cannula comprises a slot configured to secure the proximal flange of the inner cannula. In at least one embodiment, the slot extends along a portion of the proximal flange of the outer cannula; the proximal flange of the inner cannula has an obround shape; and wherein the proximal flange of the inner cannula has a thickness less than a thickness of the slot. In at least one embodiment, the device further comprises windows disposed on the annular second stem of the inner cannula at or near the proximal flange of the inner cannula, wherein the windows are configured to receive protrusions of an insertion tool, wherein the protrusions are configured to extend through the windows. In at least one embodiment, the slot has a thickness, and the proximal flange of the inner cannula has a thickness less than a thickness of the slot.

The present disclosure includes disclosure of a method of deploying a voice prosthesis device, the method comprising the steps of inserting an inner cannula into an outer cannula wherein the inner cannula comprises a stem and an obround proximal flange; the outer cannula defines a passageway configured to accept said stem; and a retaining slot disposed on a proximal flange of the outer cannula, the retaining slot extending along a portion of the proximal flange of the outer cannula; wherein the step of inserting the inner cannula into the outer cannula comprises inserting the stem into the passageway. In at least one embodiment, the method further comprises rotating the inner cannula such that the obround proximal flange is disposed within the retaining slot. In at least one embodiment, the method further comprises attaching an insertion tool to the inner cannula, wherein the inner cannula comprises windows; and the insertion tool comprises moveable protrusions configured to extend through the windows; and wherein the step of inserting the inner cannula into the outer cannula and the step of rotating the inner cannula is performed by operating the insertion tool.

The present disclosure includes disclosure of a voice prosthesis device, comprising an inner cannula comprising a distal end and a proximal flange connected by a annular second stem, the annular second stem defining a passageway therethrough; and an outer cannula comprising a distal flange and a proximal flange connected by an annular first stem, the annular first stem defining a passageway therethough. In at least one embodiment, the annular second stem fits within the annular first stem. In at least one embodiment, the annular first stem comprises retaining nubs on an inner surface of the annular first stem, and the annular second stem comprises windows. In at least one embodiment, said windows and retaining nubs are aligned with one another. In at least one embodiment, the proximal flange of the inner cannula has an obround shape, and the outer cannula defines a slot configured to secure the proximal flange of the inner cannula. In at least one embodiment, the slot has a thickness, the slot extends along a portion of the proximal flange of the outer cannula, and the proximal flange of the inner cannula has a thickness less than the thickness of the slot. In at least one embodiment, the inner cannula comprises a valve.

The present disclosure includes disclosure of a voice prosthesis device, comprising an inner cannula comprising a distal end and a proximal flange connected by a annular second stem, the annular second stem defining a passageway therethrough; an outer cannula comprising a distal flange and a proximal flange connected by an annular first stem, the annular first stem defining a passageway therethough; and windows disposed on the second annular stem at or near the proximal flange of the inner cannula. In at least one embodiment, the device comprises part of a system, the system further comprising an insertion tool configured for at least partial insertion into the windows disposed on the second annular stem. In at least one embodiment, the device comprises part of the system, and the insertion tool comprises an inner cylinder slidably disposed within an outer cylinder. In at least one embodiment, the device comprises part of the system, and the outer cylinder comprises a distal end and apertures on the distal end, and the inner cylinder comprises a distal end and protrusions that extend through the apertures. In at least one embodiment, the device comprises part of the system, and the inner cylinder has two separated ends at the distal end of the inner cylinder. In at least one embodiment, the device comprises part of the system, and the inner cylinder has a first position wherein in the first position the protrusions are retracted into the apertures. In at least one embodiment, the device comprises part of the system, and the inner cylinder has a second position wherein in the second position the protrusions are extending through the apertures. In at least one embodiment, the device comprises part of the system, and the first position is relatively distal of the second position. In at least one embodiment, the device comprises part of the system, and the inner cylinder extends from the proximal end of the outer cylinder. In at least one embodiment, the inner cannula comprises a valve.

The present disclosure includes disclosure of an insertion tool, the insertion tool configured for at least partial insertion into one or more windows defined within part of a voice prosthesis device, the voice prosthesis device comprising an inner cannula comprising a distal end and a proximal flange connected by a annular second stem, the annular second stem defining a passageway therethrough; and an outer cannula comprising a distal flange and a proximal flange connected by an annular first stem, the annular first stem defining a passageway therethough. In at least one embodiment, the insertion tool comprising an inner cylinder slidably disposed within an outer cylinder. In at least one embodiment, the inner cylinder comprises a protrusion at its distal end, the protrusion configured to be inserted into the one of more windows. In at least one embodiment, the outer cylinder comprises apertures and the protrusion can extend through the apertures into the one of more windows. In at least one embodiment, the inner cylinder comprises two separated ends at the distal end and a protrusion on each end and the outer cylinder has two complementary apertures. In at least one embodiment, the inner cylinder has a first position, and in the first position the protrusions are retracted into the apertures. In at least one embodiment, the inner cylinder has a second position, and in the second position the protrusions are extending through the apertures. In at least one embodiment, the first position is relatively distal to the second position. In at least one embodiment, the inner cylinder extends from the proximal end of the outer cylinder. In at least one embodiment, the insertion tool comprises a retaining pin, the retaining pin disposed between the two separate ends. In at least one embodiment, a spring is disposed around the inner cylinder, and the spring is compressed when the inner cylinder is in the first position. In at least one embodiment, the outer cylinder comprises a retainer, the retainer disposed in the proximal end of the outer cylinder and configured to prevent the inner cylinder from sliding out of the outer cylinder.

The present disclosure includes disclosure of a system, comprising a voice prosthesis device, comprising an inner cannula comprising a distal end and a proximal flange connected by a annular second stem, the annular second stem defining a passageway therethrough; and an outer cannula comprising a distal flange and a proximal flange connected by an annular first stem, the annular first stem defining a passageway therethough; wherein the outer cannula comprises a tab extending from the proximal flange and a hole in the tab; and an insertion tool configured to engage the voice prosthesis device. In at least one embodiment, the insertion tool comprises a peg extending therefrom. In at least one embodiment, the tab is bendable and wherein the peg can be inserted into the hole of the tab.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

Figure 1:
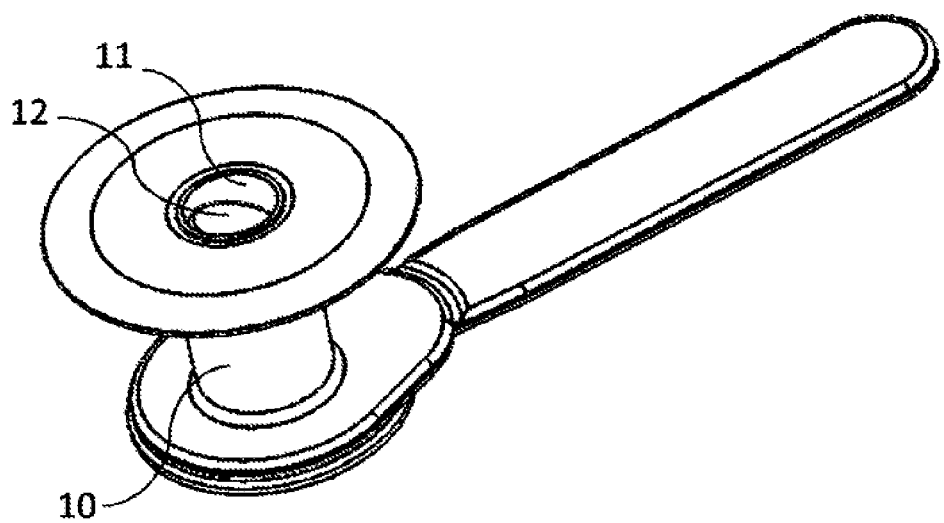
FIG. 1 is a representation of the voice prosthesis unit, according to at least one embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Furthermore, although the exemplary figures may have size markings such as French or millimeters, they intended to be merely illustrative and non-limiting. The embodiments described herein may be of any dimension.

Figure 2:
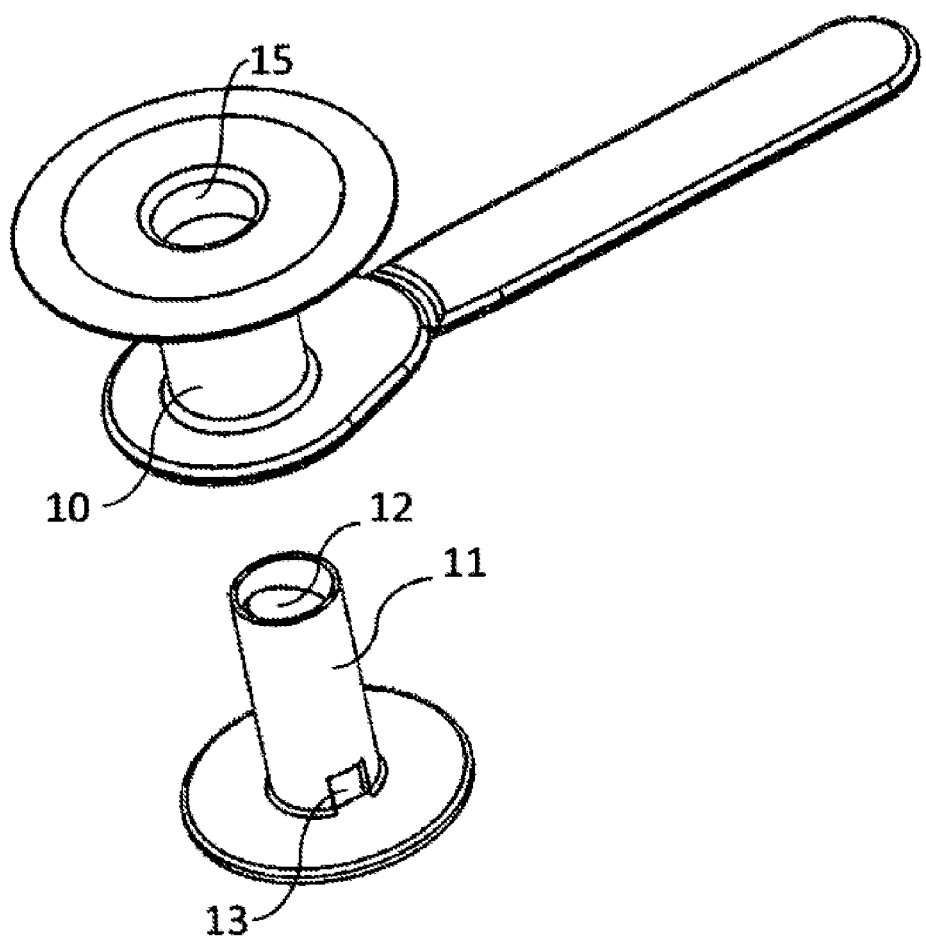
FIG. 2 is an exploded view of the voice prosthesis unit, according to at least one embodiment of the present disclosure.

Referring to FIGS. 1-5 there is shown a first embodiment of the voice prosthesis unit of the present invention, including a tubular outer cannula 10 made of a silicone rubber or a thermal plastic elastomer and a removable tubular inner cannula 11 made of a rigid plastic material, shown removed in FIG. 2. The outer cannula 10 is for insertion into the fistula, i.e. a passage between trachea and esophagus of the patient through an opening in the neck and has a flange and opening at both distal and proximal ends.

Figure 3:
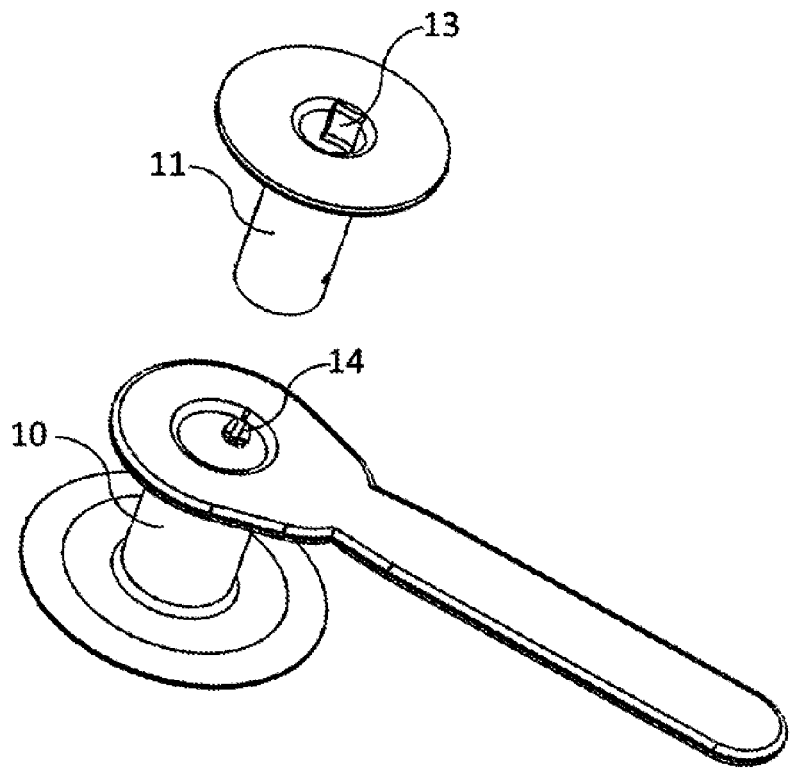
FIG. 3 is also an exploded view of the voice prosthesis unit, according to at least one embodiment of the present disclosure.
Figure 4:
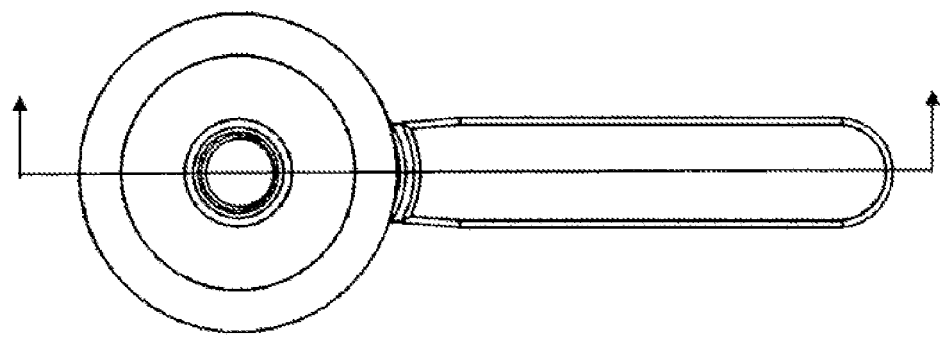
FIG. 4 is a top view of the voice prosthesis unit, according to at least one embodiment of the present disclosure.

The inner cannula 11 is inserted into the proximal opening of the outer cannula 10 and secured in place by means of a coupling feature located on its proximal end as shown in FIG. 3. The coupling feature is a pair of windows 13 which engage retaining nubs 14 located on the proximal end of the outer cannula 10. The windows 13 can be connected to an insertion tool, not shown.

The outer cannula 10 is made of a compliant material such as silicone rubber or a thermal plastic elastomer material and therefore the retaining nubs 14 of the outer cannula 10 are compliant and will move out of the way as the rigid plastic inner cannula 11 is inserted. The inner cannula 11 has windows 13 that when placed in the desired position within the outer cannula 10 will allow the nubs 14 to spring back into its molded shape. Further the outer cannula has a reduced diameter portion 15 near its esophageal end as shown in FIG. 2, and the inner cannula surface 11 abutting against the reduced diameter portion 15 on the outer cannula when the inner cannula is inserted into the outer cannula forms a gas seal means for preventing leakage of gas from the voice prosthesis.

Figure 5:
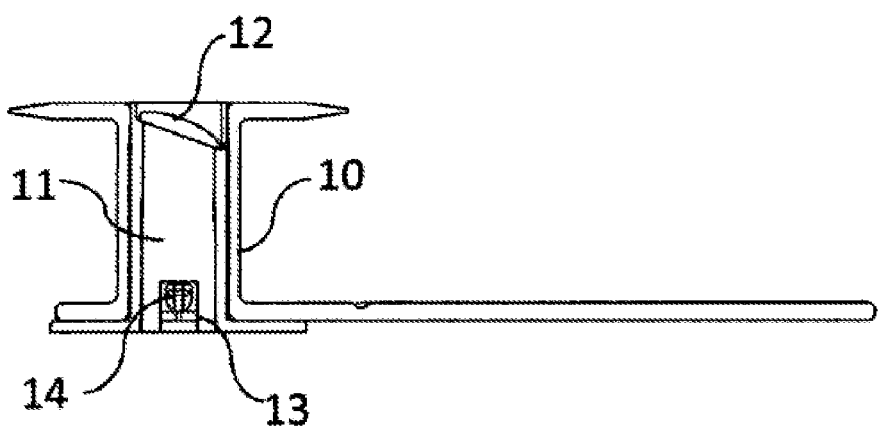
FIG. 5 is a sectional view of the voice prosthesis unit, according to at least one embodiment of the present disclosure.
Figure 6:
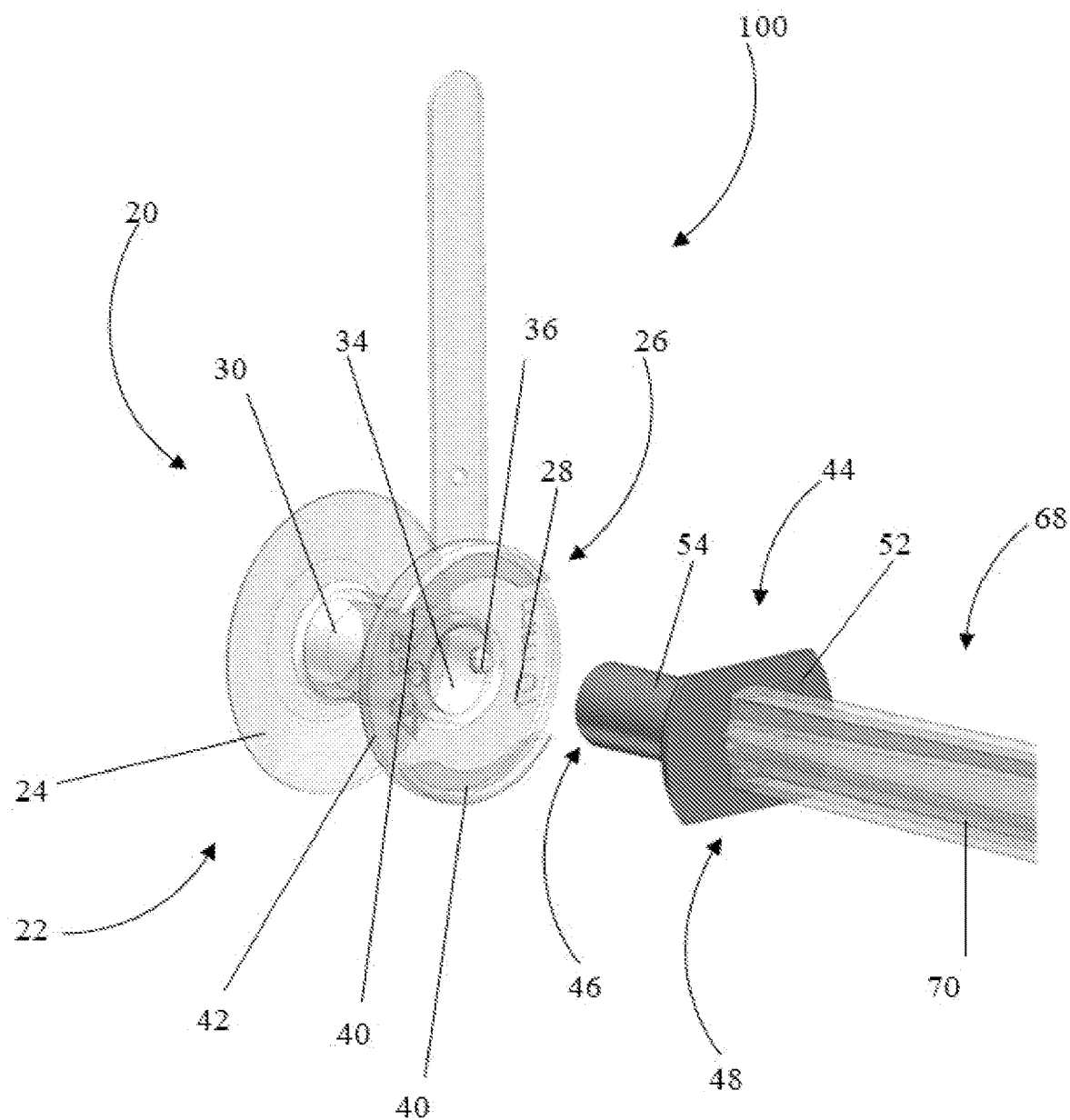
FIGS. 6, 7, 8, and 9 show the process of deploying an embodiment of the voice prosthesis unit, according to at least one embodiment of the present disclosure.
Figure 7:
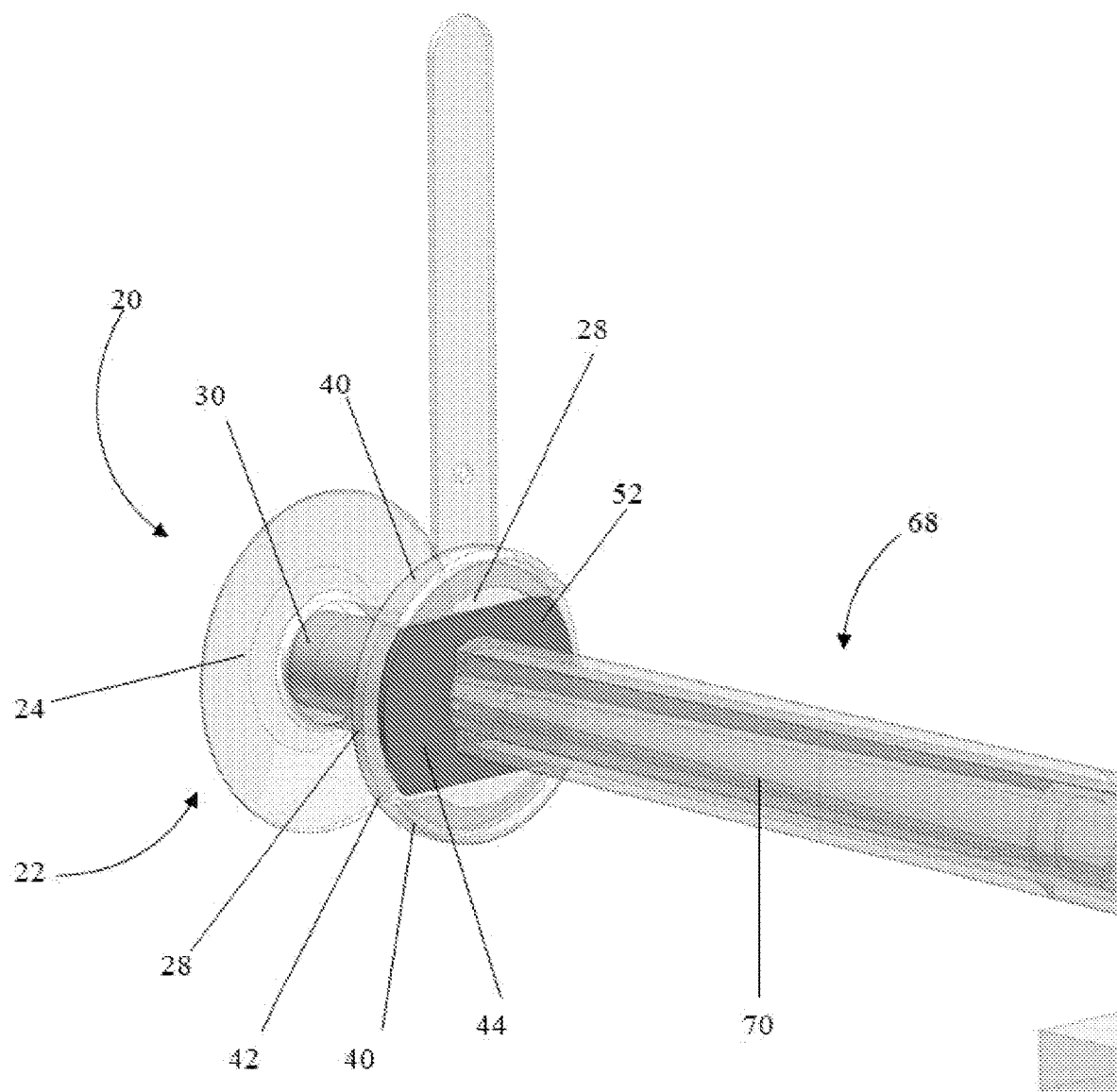
Figure 8:
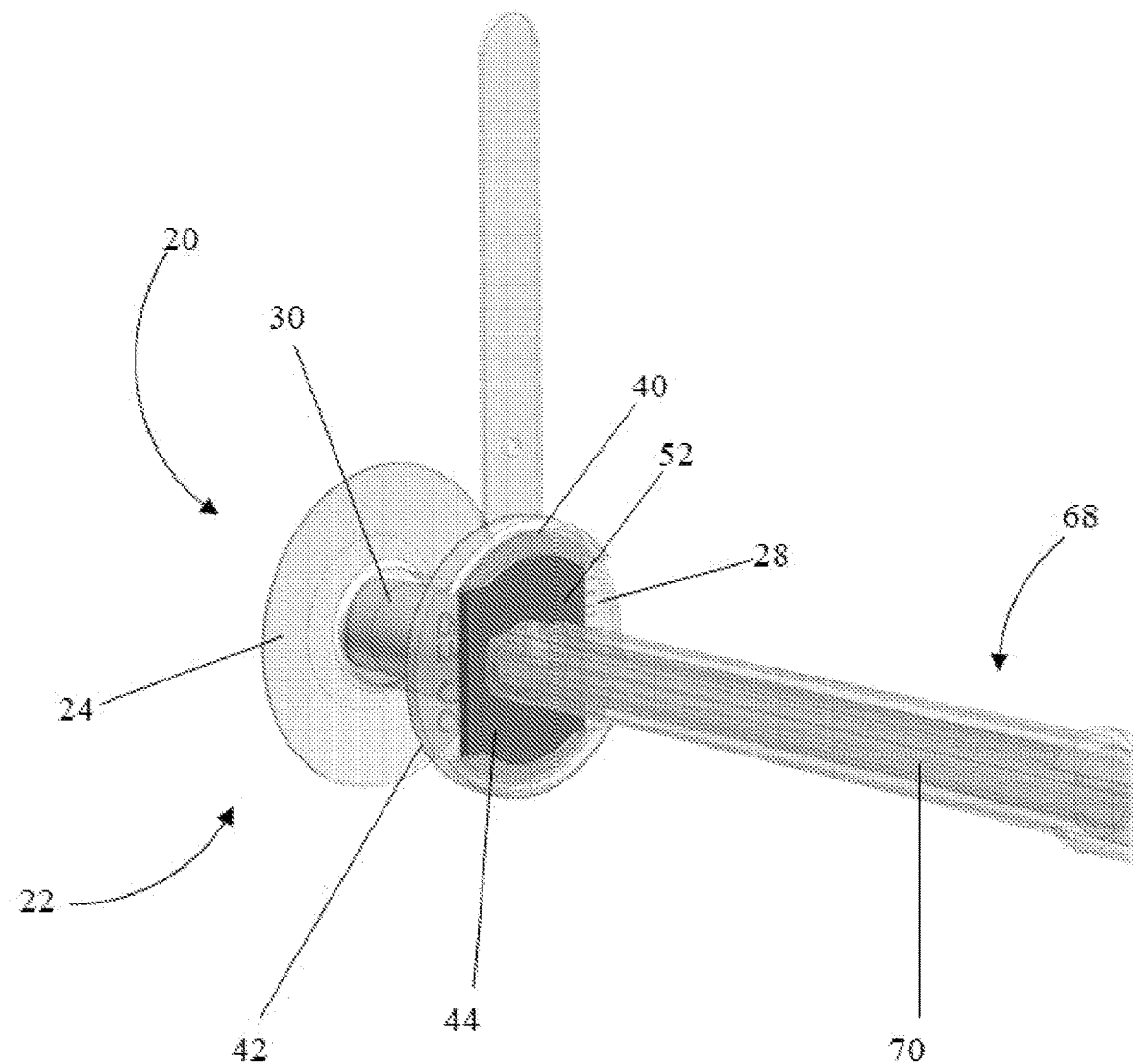
Figure 9:
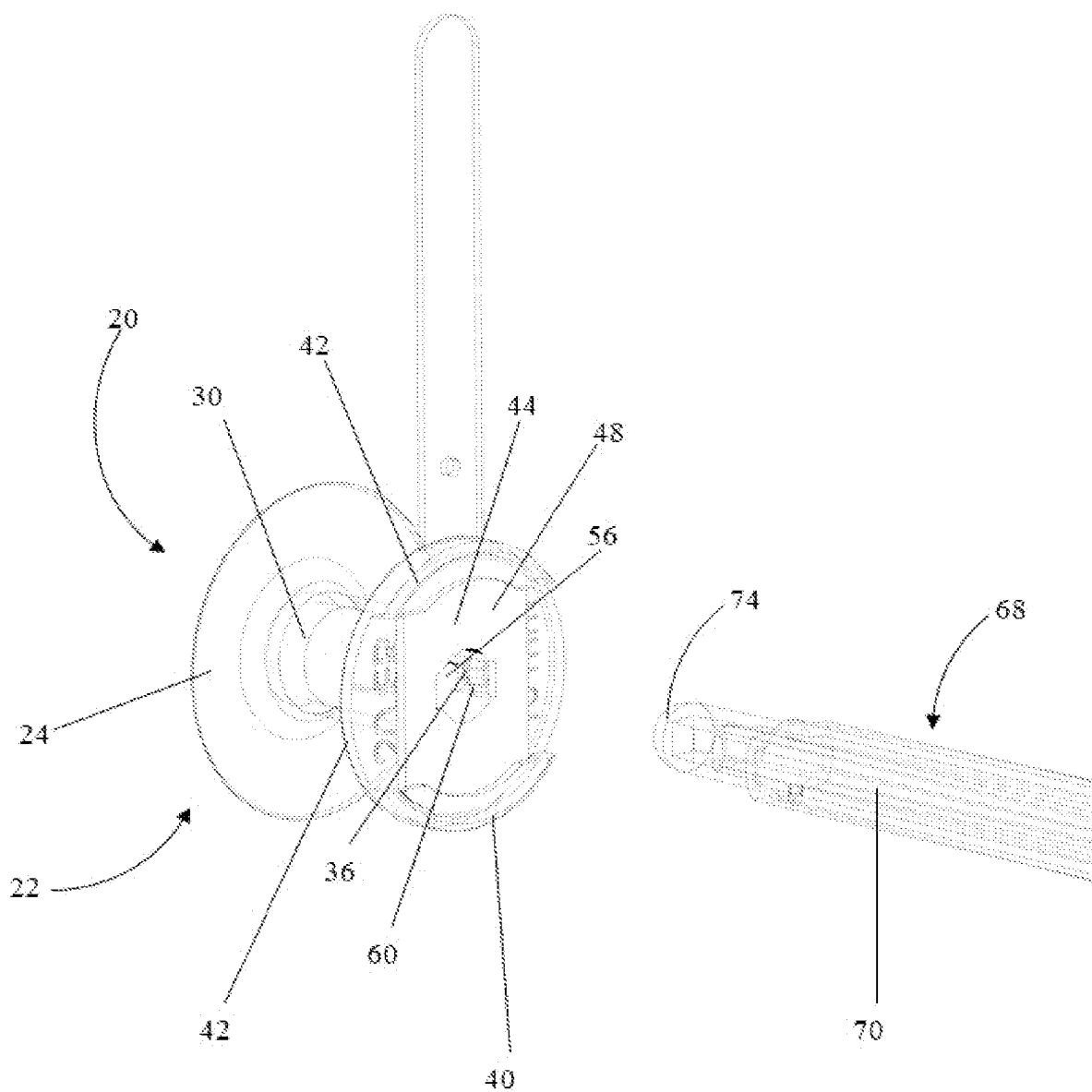
Figure 10:
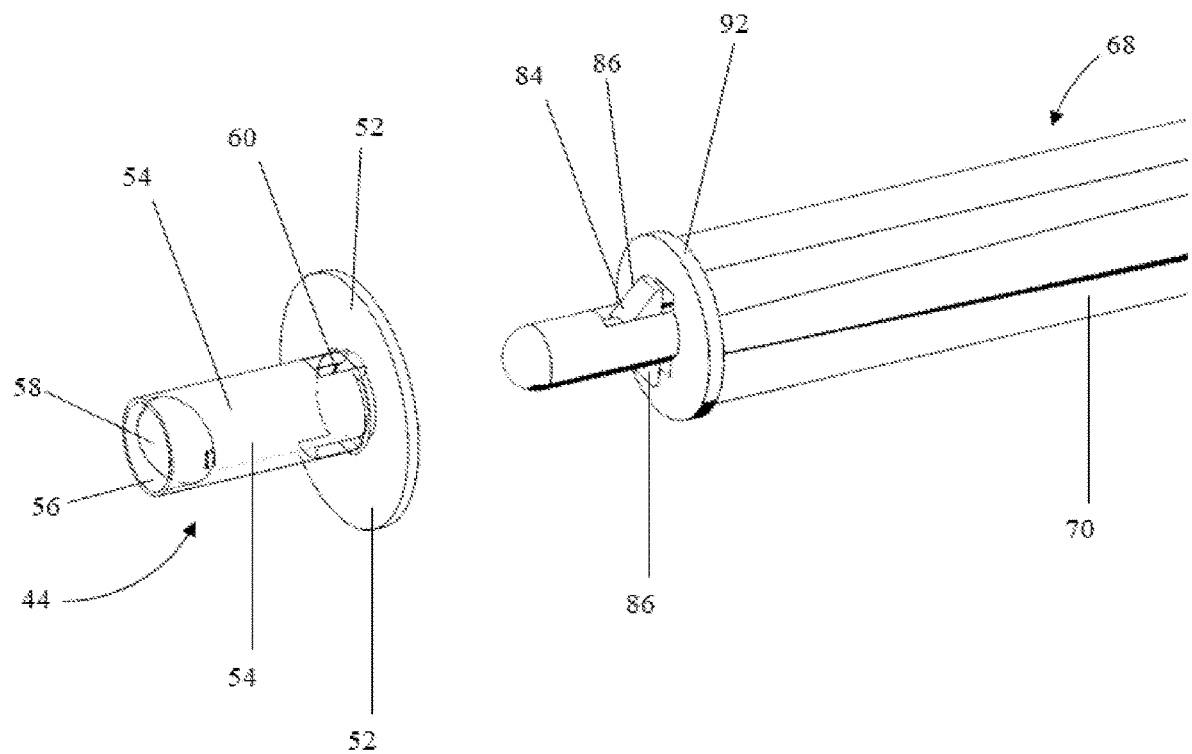
FIG. 10 is a semitransparent view of an inner cannula and the distal end of the insertion tool, according to at least one embodiment of the present disclosure.
Figure 11:
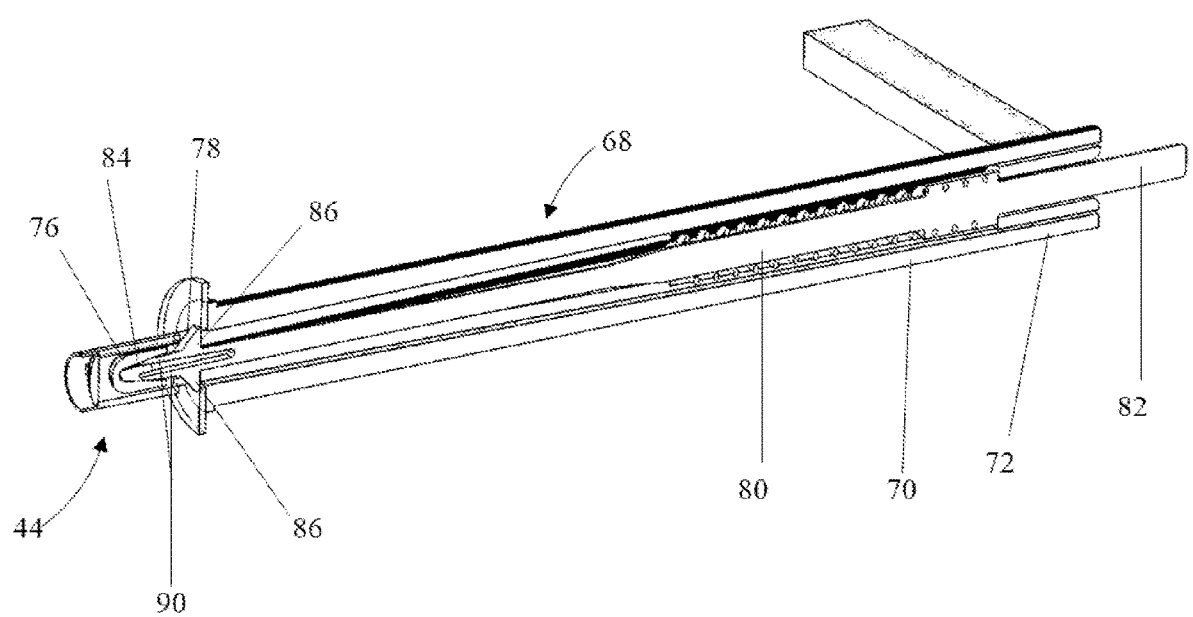
FIG. 11 is a sectional view of the insertion tool attached to the inner cannula, according to at least one embodiment of the present disclosure.

The inner cannula 11 forms a passageway to permit air to flow from the trachea into the esophagus. FIG. 5 is a sectional view of the voice prosthesis unit of the present invention. Mounted and located just at the distal end behind the tip of the inner cannula 11 is a flap valve 12.

An important feature of the inner cannula 11 of the present invention, is its disposability, it is relative in expense associated with the polymer materials and methods of manufacture from which it is constructed. For example, the inner cannula 11 can be quickly and easily produced in large quantities using an injection molding or extrusion molding process and then end-formed to create the flange at the proximal end using a heating and forming process.

Furthermore, dimensional tolerances are held close only in the distal area of the inner cannula 11 and outer cannula 10 to assure an adequate seal. This provides for ease of insertion of the inner cannula 11 into the outer cannula 10 and interchangeability of the inner cannula 11.

Furthermore, as described above, these inner cannulas 11 are sufficiently economical in terms of material and manufacturing cost to make their disposability practical. The inner cannula 11 with incorporated flap valve 12 can be removed, cleaned, or disposed of making it easy to replace when in case of an obstructed flap valve 12. Thus, adding to the longevity of the outer cannula 10 and reducing the frequency of replacement needed.

In a second embodiment as pictured in FIGS. 6-13, the invention comprises a inner cannula 44, and outer cannula 20 as generally described above and also including the additional features below.

Referring to FIGS. 6-13, the outer cannula 20 has a general spool-like shape comprising a distal end 22, a distal flange 24 thereupon, a proximal end 26, a proximal flange 28 thereupon and a hollow outer cannula stem 30 connecting the distal 24 and proximal flanges 28. The distal flange 24 and the proximal flange 28 are circular in shape, but may take any shape. The distal flange 24 and the proximal flange 28 are connected by the stem 30, the stem 30 comprising a passageway 34 therethough. As a result, the stem 30 is annular in shape, or described another way, takes the shape of hollow cylinder. The passageway 34 has a smaller diameter near the outer cannula distal end, thereby forming a reduced diameter portion 32. The length of the stem 30 is such that it may be deployed in the fistula between a trachea and an esophagus in accordance with the purpose of the invention. The distal flange 24 and the proximal flange 28 have a larger diameter than the stem 30. This prevents dislodging of the outer cannula 20 after deployment. The outer cannula 20 may be made of a silicone rubber or a thermal plastic elastomer or any suitable soft or compliant material.

The inner cannula 44 comprises a distal end 46 connected to a proximal end 48 and a proximal flange 52 via an inner cannula stem 54. The inner cannula distal end 46 and the inner cannula proximal flange 52 are connected by a stem 54 having a passageway 56 therethrough. The distal end 46 of the inner cannula 44 is sized to fit within the outer cannula passageway 34 to form a gas seal preventing leakage from the voice prosthesis 100. For example, the length of the inner cannula 44 is approximately equal to the length of the outer cannula 20 and the inner cannula 44 may abut against the outer cannula reduced diameter portion 32 disposed near the distal end 22 of the outer cannula 20. The inner cannula proximal flange 52 may take any shape, and in this embodiment is an obround shape having a diametric dimension larger than the stem 54 diameter as shown in FIGS. 6-9. A flap valve 58 may be located in the distal end 46 of the inner cannula 44.

The outer cannula 20 is configured to secure the inner cannula 44. The inner cannula stem 54 comprises windows 60 at or near its proximal end 48. The outer cannula 20 further comprises at least one retaining nub 36 at or near the outer cannula proximal end 26. The at least one retaining nub 36 is sized to extend through the inner cannula windows 60 so that when the inner cannula stem 54 is inserted into the outer cannula passageway 34, the at least one retaining nub 36 will secure the inner cannula 44 in place via the windows 60. The at least one retaining nub 36 may comprise a bevel 38 to aid in sliding the inner cannula stem 54 over the at least one retaining nub 36.

The outer cannula 20 may also secure the inner cannula 44 via a slot 40 disposed on the outer circumferential edge 42 of the outer cannula proximal flange 28 as shown in FIGS. 6-9. A wall 62 extends perpendicularly and in a proximal direction from the outer circumferential edge 42 of the outer cannula proximal flange 28. The wall 62 is further connected to an overhang 64 which extends parallel to the proximal flange 28 and extends toward the longitudinal axis of said proximal flange 28. The slot 40 comprises the space surrounded by the proximal flange 28, the wall 62 and the overhang 64. The wall and overhang extend along a portion of the proximal flange circumference 42 and the overhang extends only partially toward the longitudinal axis. The distance between the proximal flange and the overhang, i.e. the thickness of the slot 40, is larger than the thickness of the inner cannula proximal flange 52.

In the embodiment pictured in FIGS. 6-9, the slot comprises two approximately 90 degree arcs of the outer cannula proximal flange 28, disposed at the top and bottom of the outer cannula proximal flange 28, approximately 180 degrees from each other. To secure the inner cannula 44 to the outer cannula 20, the stem 54 of the inner cannula 44 is inserted into the passageway 34 of the outer cannula 20 until the proximal flanges 28, 52 of the two cannulas 20, 44 are contacting each other. An obround inner cannula proximal flange 52 would be placed 90 degrees from the slot 40 as the overhang would otherwise prevent the two proximal flanges 28, 52 from contact. Once the two proximal flanges 28, 52 are in contact, the inner cannula 44 is then rotated 90 degrees so that the obround proximal flange 52 of the inner cannula 44 slides into and is disposed in the slot 40. In this manner the inner cannula 44 is secured to the outer cannula 20 via rotation of the inner cannula 44. This may be also referred to as a "bayonet locking feature."

The slot 40 and the inner cannula proximal flange 52 may have a friction fit. In another embodiment, the outer cannula 20 may be comprised of a material softer than the inner cannula 44. For example, the outer cannula 20 may be a soft silicone of thermal plastic elastomer and the inner cannula 44 may be a harder rigid plastic.

In a further embodiment, the outer cannula 20 comprises the retaining slot 40, but not the retaining nubs 36 and inner cannula windows 60 combination.

The deployment of the inner cannula may be done with an insertion tool 68 configured to secure to the inner cannula 44 as pictured in FIGS. 6-13. The insertion tool 68 comprises two concentric cylinders, an outer cylinder 70 housing an inner cylinder 80 within. The outer cylinder 70 comprises a proximal end 72 and a distal end 74, the distal end 74 having a diameter smaller than the diameter of the inner cannula passageway 56. The outer cylinder 70 also has at least one aperture 78 at or near the distal end 74. The outer cylinder 70 may also comprise a flange 92 between the outer cylinder distal end 74 and the outer cylinder proximal end 72, the flange 92 having a larger diameter than the outer cylinder distal end 74 and outer cylinder proximal end 72.

The inner cylinder 80 comprises a proximal end 82 which is operable by a practitioner. For example the inner cylinder proximal end 82 may extend from the outer cylinder proximal end 72 so that a practitioner may apply pressure to the extending inner cylinder proximal end 82 such that it slides into the outer cylinder 70. The inner cylinder 80 also comprises at least one protrusion 86 at or near its distal end 84 which extend through the at least one apertures 78 of the outer cylinder 70. In the pictured embodiments, the inner cylinder 80 comprises two protrusions 86 and the outer cylinder comprises two associated apertures 78. The protrusions 86 of the inner cylinder 80 may also have a bevel 88.

Figure 12:
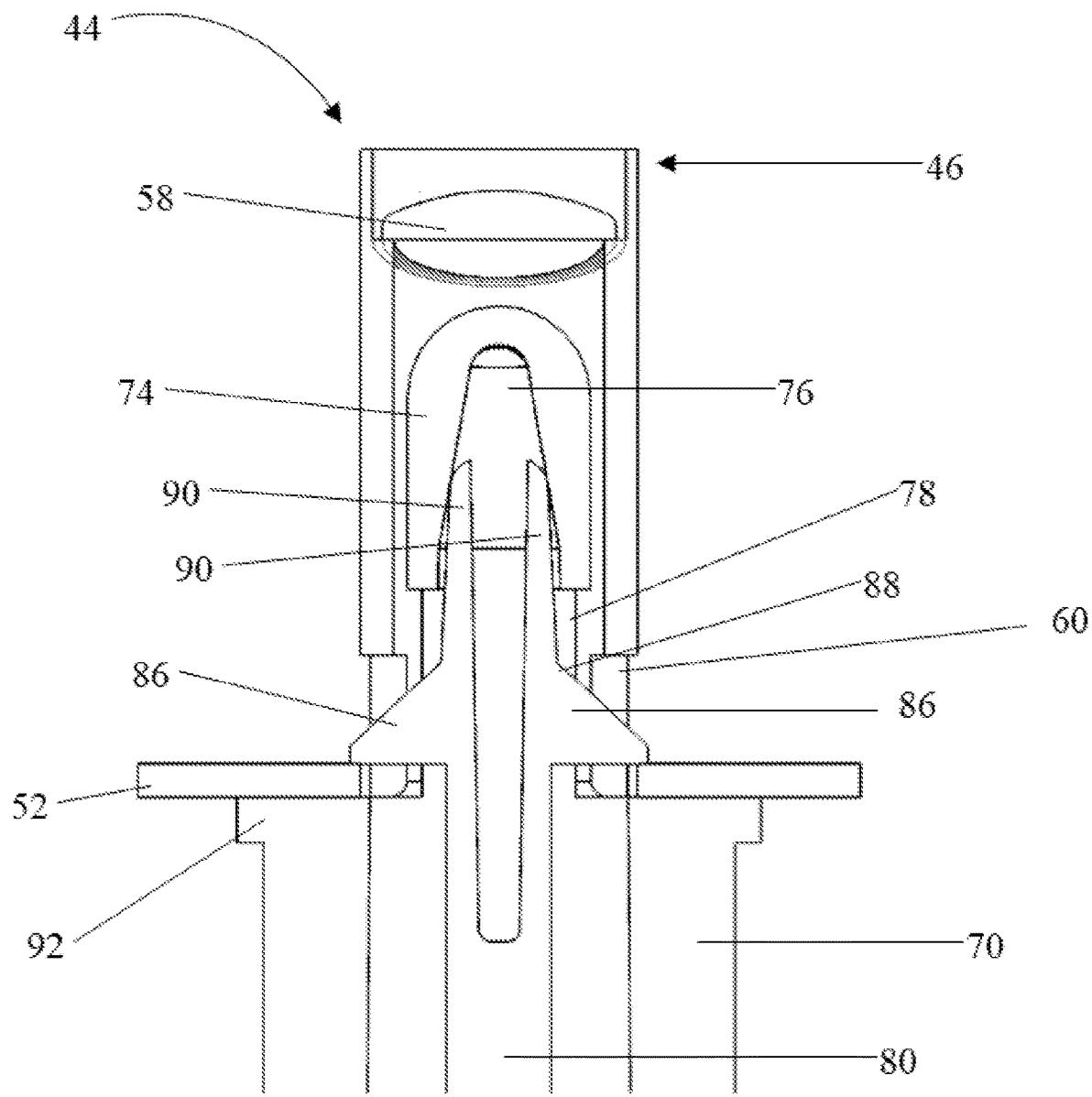
FIG. 12 is a close up sectional view of the insertion tool attached to the inner cannula, according to at least one embodiment of the present disclosure.

Referring to FIG. 12, the distal end 74 of the outer cylinder 70 has a taper 76 where the inner cylinder 80 is housed within. The distal end 84 of the inner cylinder 80 is comprised of two separated ends 90. Thus when a practitioner applies pressure to the inner cylinder proximal end 82, the inner cylinder distal end 84 will move into the taper 76, and the two separated ends 90 will be pressed together. This causes the protrusions 86 to withdraw from the apertures 78.

The inner cannula 44 can be attached to the insertion tool 68 via its windows 60. In one method of doing so, the protrusions 86 of the inner cylinder 80 can be withdrawn by pressing the inner cylinder distal end 84. The practitioner can then align the windows 60 of the inner cylinder 80 with the protrusions 86. Releasing the inner cylinder 80 will extend the protrusions 86, securing the inner cylinder 80 in place.

In an alternate method the protrusions are beveled 88 and the inner cannula 44 can simply be slid onto the inner cannula 44. The hard inner cannula stem 54 will force the protrusions 86 to withdraw at least partially into the outer cylinder 70 until aligned with the windows 60. Once the protrusions 86 and windows 60 are aligned, the protrusions 86 will be free to extend outward and through the windows 60, securing the inner cannula 44 to the insertion tool 68.

The resulting insertion tool 68 and inner cannula 44 assembly can be used to place the inner cannula 44 onto the outer cannula 20. While holding the insertion tool 68, the practitioner can slide the inner cannula 44 into the outer cannula 20, aligning the retaining nubs 36 and the windows 60. The practitioner can then press the distal end 84 of the inner cylinder 80 which withdraws the protrusions 86 and releases the inner cannula 44. The insertion tool 68 can then be removed leaving the inner cannula 44 deployed within the outer cannula 20.

Although FIGS. 10-13 show a circular inner cannula proximal flange 52, the insertion tool 68 may also be used with an inner cannula 44 having a obround proximal flange 52 as in FIGS. 6-9, or any other shape.

Figure 13:
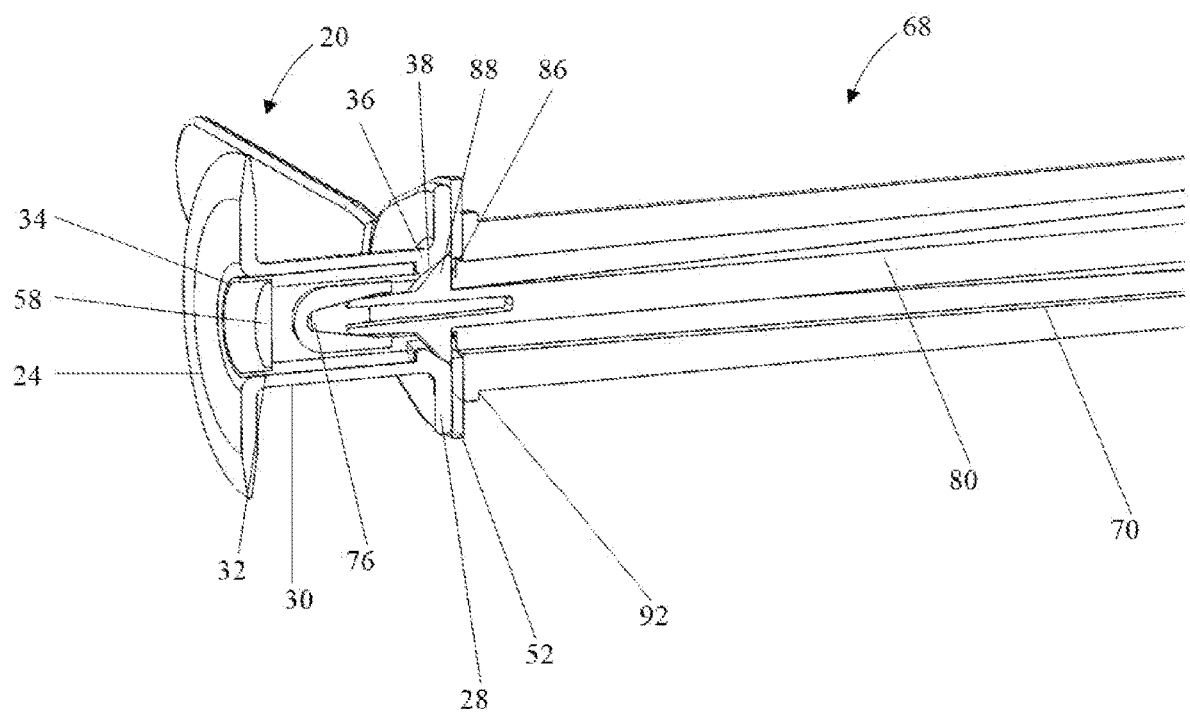
FIG. 13 is a sectional view of the insertion tool attached to the inner cannula and outer cannula, according to at least one embodiment of the present disclosure.

FIG. 13 shows that the retaining nubs 36 and the protrusions 86 are beveled in complimentary directions so that both the retaining nubs 36 and the protrusions 86 fit within the window 60 simultaneously.

As illustrated in FIGS. 6, 7, 8, and 9, the insertion tool 68 and inner cannula 44 assembly can also be used to secure the inner cannula 44 to the outer cannula 20 when the inner cannula proximal flange 52 is obround. As described in the second embodiment, the obround proximal flange 52 is placed 90 degrees from the slot 40. While grasping the insertion tool 68, the practitioner can rotate the insertion tool 90 degrees. This causes rotation of the inner cannula 90 degrees and securing it within the slot 40. The practitioner can then depress the inner cylinder distal end 84 to release the inner cannula 44 from the insertion tool 68.

The insertion tool 68 can be used to remove the inner cannula 44. The insertion tool 68 is inserted into the inner cannula 44. The inner cylinder 80 is then released, extending the protrusions 86 and securing the inner cannula 44 to the insertion tool 68.

The practitioner can then manipulate the inner cannula 44 for removal, either by sliding the inner cannula 44 outward over the retaining nubs 36, or by first rotating the insertion tool 90 degrees and the sliding the inner cannula 44 away from the outer cannula 20, depending on how the inner cannula 44 is secured.

Figure 14:
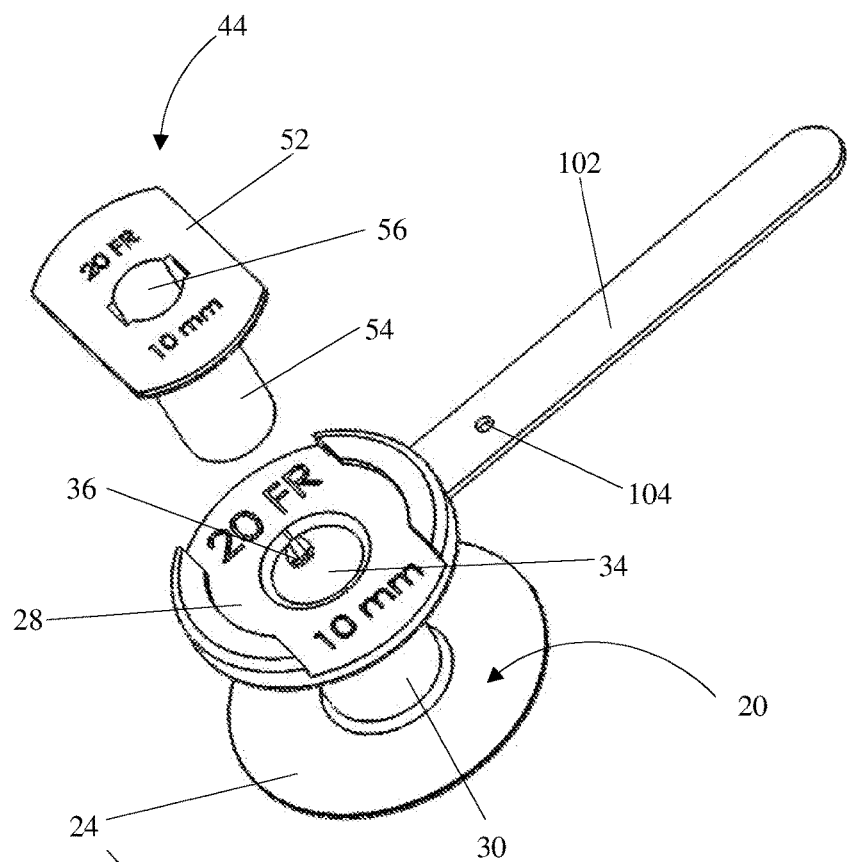
FIG. 14 is an exploded view of the voice prosthesis unit, according to at least one embodiment of the present disclosure.
Figure 15:
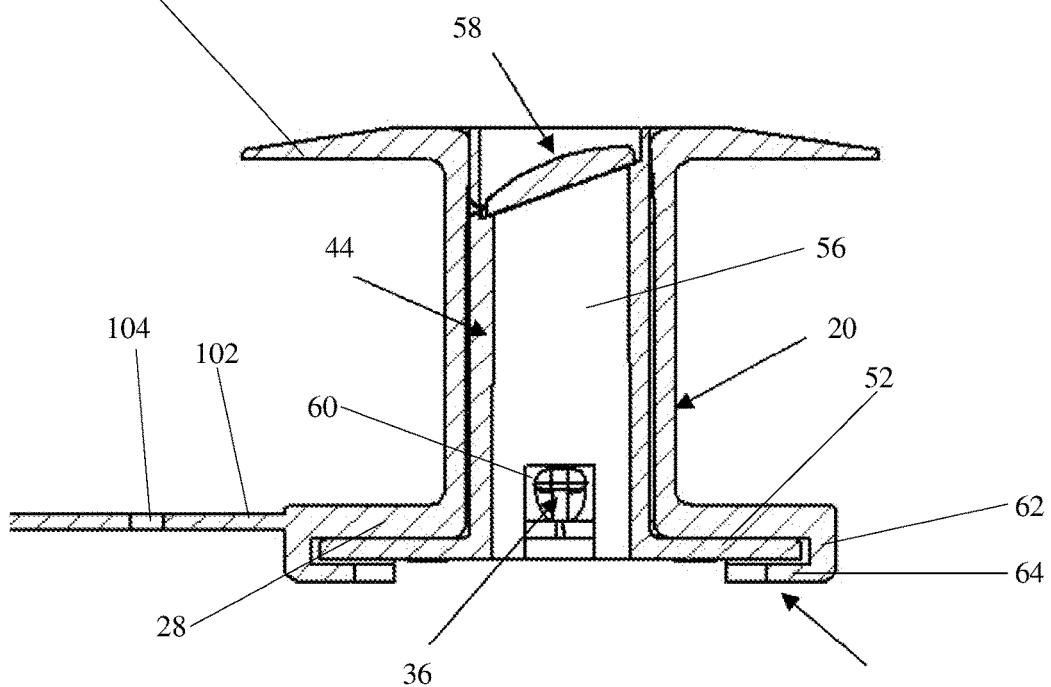
FIG. 15 is a sectional view of the voice prosthesis unit, according to at least one embodiment of the present disclosure.
Figure 16:
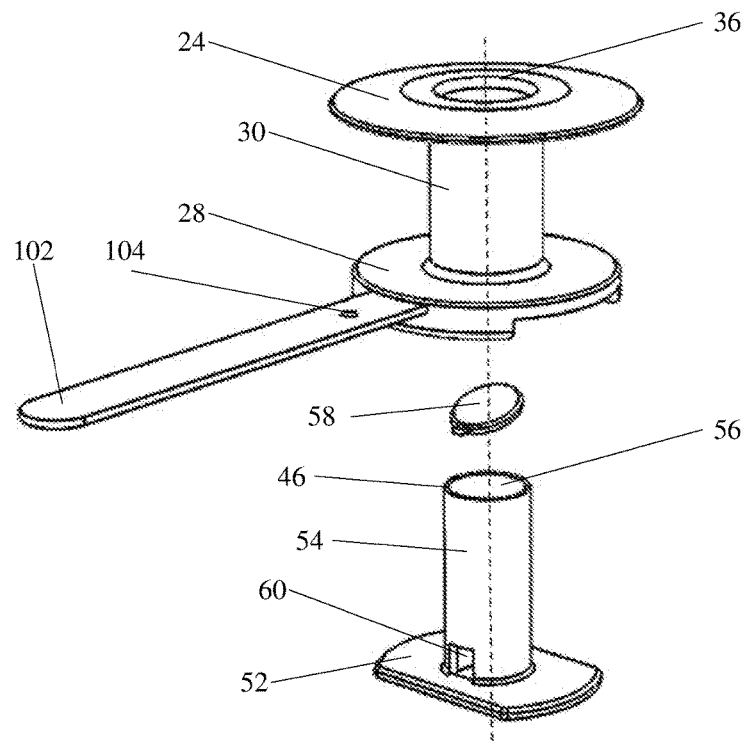
FIG. 16 is an exploded view of the voice prosthesis unit, according to at least one embodiment of the present disclosure.

FIGS. 14-16 show an embodiment of the inner cannula 44 and outer cannula 20 having a slot 40 for accepting an obround inner cannula proximal flange 52. This may also be known as a bayonet locking feature.

The outer cannula 20 is preferably made of a crystal clear material so the underlying tissue can be seen for evaluation. Material for the outer cannula 20 is preferably of a resilient material such as silicone rubber. As shown in FIG. 15, the inner cannula 44 comprises a stem 54 which may slide into the passageway 34 of the outer cannula 20. The inner cannula 44 preferably slides into the outer cannula 20 with minimal friction and this can be controlled by material selection and surface finish. Material for the inner cannula 44 is preferably a ridged material such as PPS or PC.

Now referring to FIGS. 15-16, in this embodiment, a flap valve 58 is disposed on the distal end 46 of the inner cannula stem 54 and is hinged at one point. The valve 58 is biased in a closed position and the valve 58 may rest at an angle on the inner cannula distal end 46 to aid this bias. Material for the valve 58 should be of a resilient material such as silicone rubber.

FIG. 15 also shows a sectional view of an inner cannula 44 deployed in an outer cannula 20. The bayonet locking feature can also be seen. The proximal flange 28 of the outer cannula 20 comprises a wall 62, which extends perpendicularly. The wall 62 then comprises an overhang 64 which extends parallel to the proximal flange 28 and toward the passageway 34 thereby forming a slot 40 between the proximal flange 28 and the overhang 64. The proximal flange 52 of the inner cannula 44 is secured by way of being disposed within the slot 40.

The inner cannula 44 is additionally secured within the outer cannula 20 via a locking feature comprising the windows 60 of the inner cannula and the retaining/locking nubs 36 of the outer cannula 20. Referring again to FIG. 15, the retaining nubs 36 are disposed on the inner surface of the cylindrical stem 30 of the outer cannula 20 and protrude into the passageway 34 of the outer cannula 20. The inner cannula 44 comprises windows 60 sized and shaped to accept the nubs 36. As the inner cannula 44 is inserted into the outer cannula 20 the nubs 36 slide longitudinally along the inner cannula stem 54 until they are circumferentially aligned with the windows 60. The inner cannula 44 is then rotated, engaging the bayonet locking feature described above, and simultaneously the nubs 34 slide circumferentially until aligned with the windows 60. As the inner cannula stem 54 and the outer cannula passageway 34 are a close fit, the nubs 36 will protrude through the windows 60 thereby engaging the windows 60 and securing the inner cannula 44 and outer cannula 20 together.

In this embodiment the nubs 36 and windows 60 are located near the proximal end 26, 48 of the outer cannula 20 and inner cannula 44, respectively. However, it is envisioned in other embodiments the nubs 36 and windows 60 could be placed more distal as long as they as positioned to secure the inner cannula 44 and the outer cannula 20 when in a fully deployed position. That is, the windows and nubs 36 would not engage the windows 60 until the proximal flanges 28, 52 of the inner cannula 44 and outer cannula 20 contact.

Figure 17:
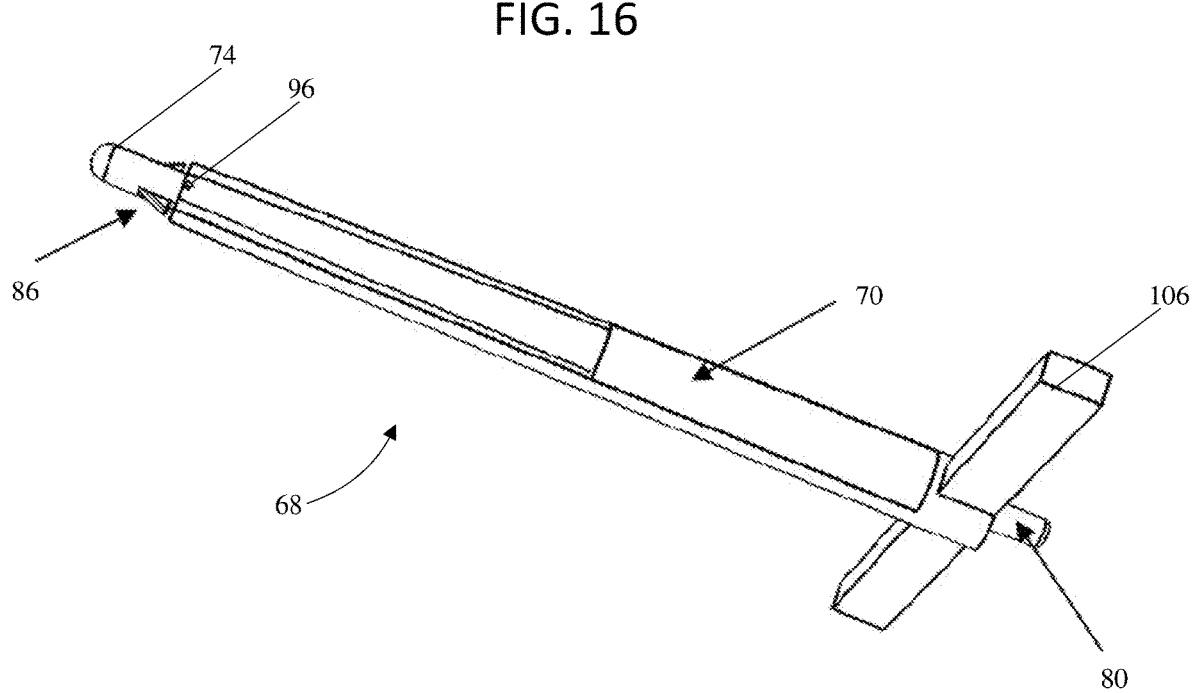
FIG. 17 is a sectional view of the insertion tool attached to the inner cannula, according to at least one embodiment of the present disclosure.
Figure 18:
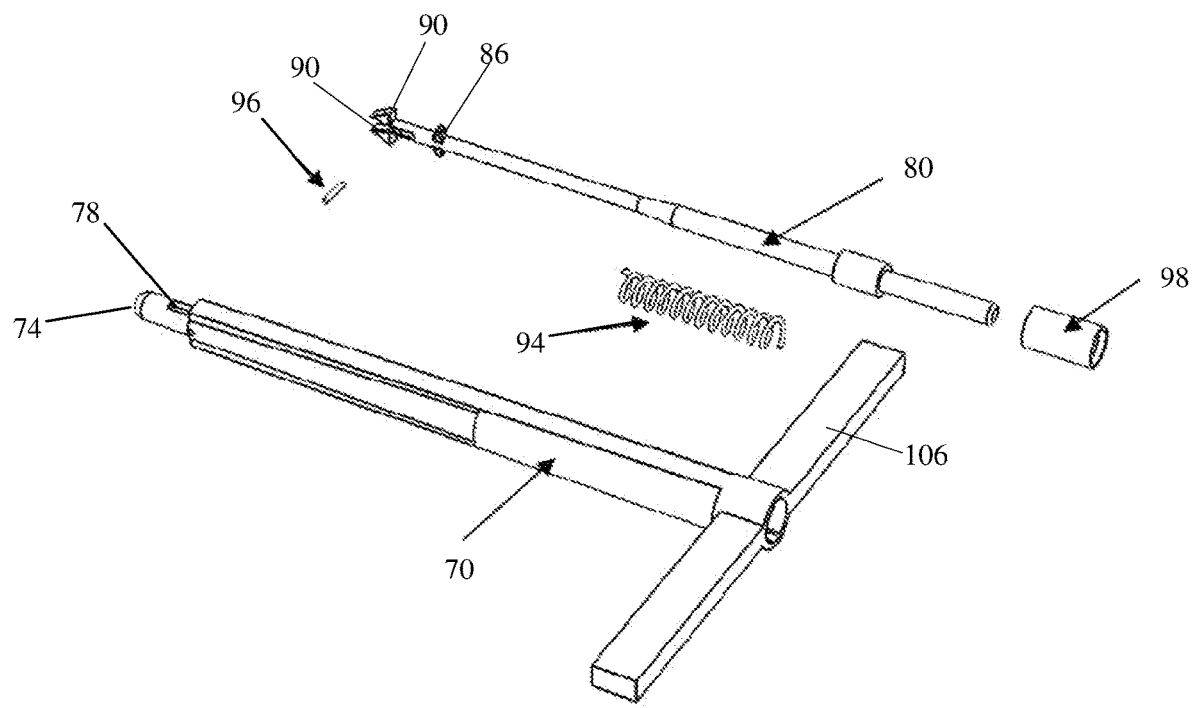
FIG. 18 is an exploded view of the insertion tool attached to the inner cannula, according to at least one embodiment of the present disclosure.

FIGS. 17 and 18 show an embodiment of the insertion tool 68 according to the present invention. The insertion tool 68 of this embodiment is similar in structure to the previously described embodiments and functions similarly. The insertion tool comprises an outer cylinder 70 having a proximal end 72 and a distal end 74 and apertures 78 in the outer cylinder distal end 74. The outer cylinder 70 may have a T-handle 106 at the proximal end to aid in grip and rotation. The insertion tool 68 also comprises an inner cylinder 80 having a proximal 82 and distal end 84 being slidably disposed inside the outer cylinder 70. The inner cylinder 80 is manipulable in a longitudinal manner and may protrude from the proximal end 82 of the outer cylinder 72. In this case, the portion of the inner cylinder 80 extending from the outer cylinder 70 may be pressed distally into the outer cylinder 70. The insertion tool may comprise a spring 94, disposed around the inner cylinder 80. The inner cylinder 80 comprises beveled protrusions 86 that may extend through the apertures 78. The inner cylinder distal end 84 may comprise two separated ends 90. A retainer 98 may also be present which keeps the inner cylinder from exiting the proximal end of the outer cylinder. The retainer 98 may be disposed at the proximal end of the outer cylinder.

Figure 19:
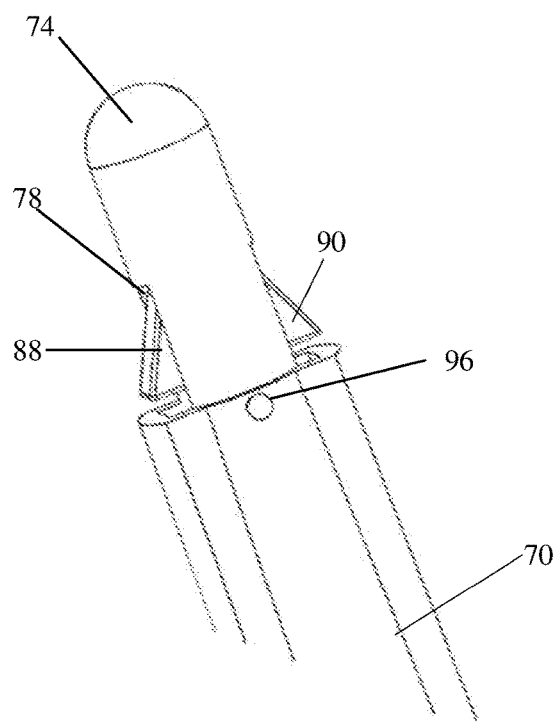
FIG. 19 is a perspective view of a distal end of an insertion tool, according to at least one embodiment of the present disclosure.
Figure 20:
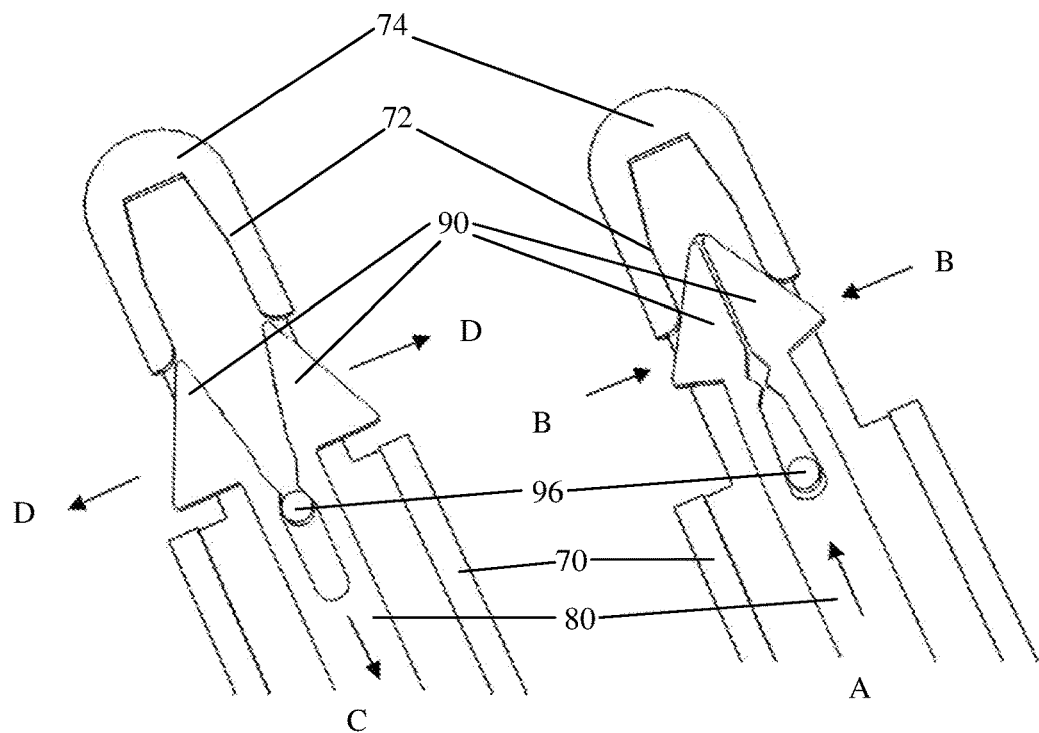
FIG. 20 is a sectional view of a distal end of an insertion tool, according to at least one embodiment of the present disclosure.

As shown in FIGS. 18-20, the insertion tool may also comprise a retaining pin 96 in the distal end. The retaining pin 96 is disposed between the two separated ends 90 of the inner cylinder 80 and may act as a stop or a guide for the inner cylinder. As the retaining pin 96 is disposed between the two separated ends 90, the inner cylinder may not be moved past the retaining pin 96.

Also shown in FIGS. 18-20, the insertion tool 68 may comprise a spring, disposed around the inner cylinder. The spring 94 functions to return the inner cylinder 80 to a initial state. In this embodiment, the portion of the inner cylinder 80 extending from the outer cylinder 70 may be pressed distally into the outer cylinder 70. For example, a clinician can use a thumb to press the inner cylinder 80 in a plunging manner to move the inner cylinder 80 distally. As the inner cylinder 80 is moved distally relative to the outer cylinder 70 (in the direction of arrow A in FIG. 20), the spring 94 compresses. The protrusions 86 on the two separated ends 90 are forced inward due to their bevel 88 and the taper of the outer cylinder proximal end 76 (arrows B). Upon releasing the inner cylinder 80, the spring 94 will uncompress pushing the inner cylinder 80 relatively proximally (arrow C). The protrusions 86 will be free to extend outward (arrows D).

Figure 21:
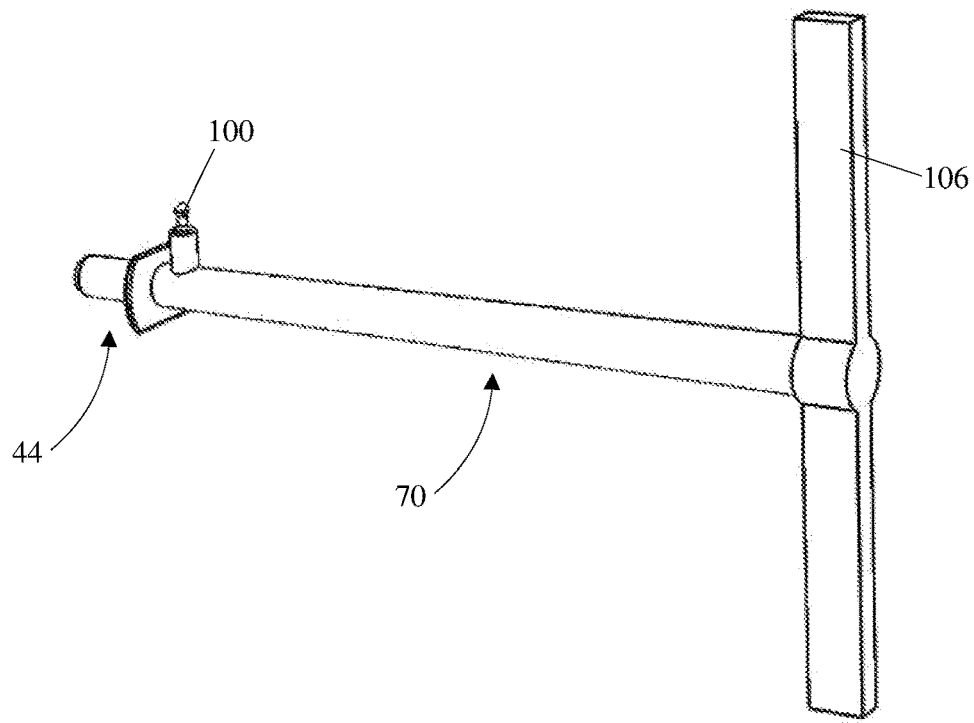
FIG. 21 is a perspective view of an insertion tool, according to at least one embodiment of the present disclosure.

The insertion tool 68 may be used to deploy a inner cannula 44 of the present invention into an outer cannula 20 of the present invention, as described previously. Now referring to FIG. 22-25, the movement of the inner cylinder 80, and therefore the movement of the protrusions 86, allows the insertion tool 68 to be placed into the inner cannula 44 to aid in deployment. The proximal end 72 of the outer cylinder fits within the passageway 56 of the inner cannula 44. The protrusions 86 are disposed to align with the windows 60 of the inner cannula 44. Thus, the protrusions 86 can extend through the windows 60 of the inner cannula 44 thereby securing the insertion tool 68 to the inner cannula 44 as in FIG. 21.

Figure 22:
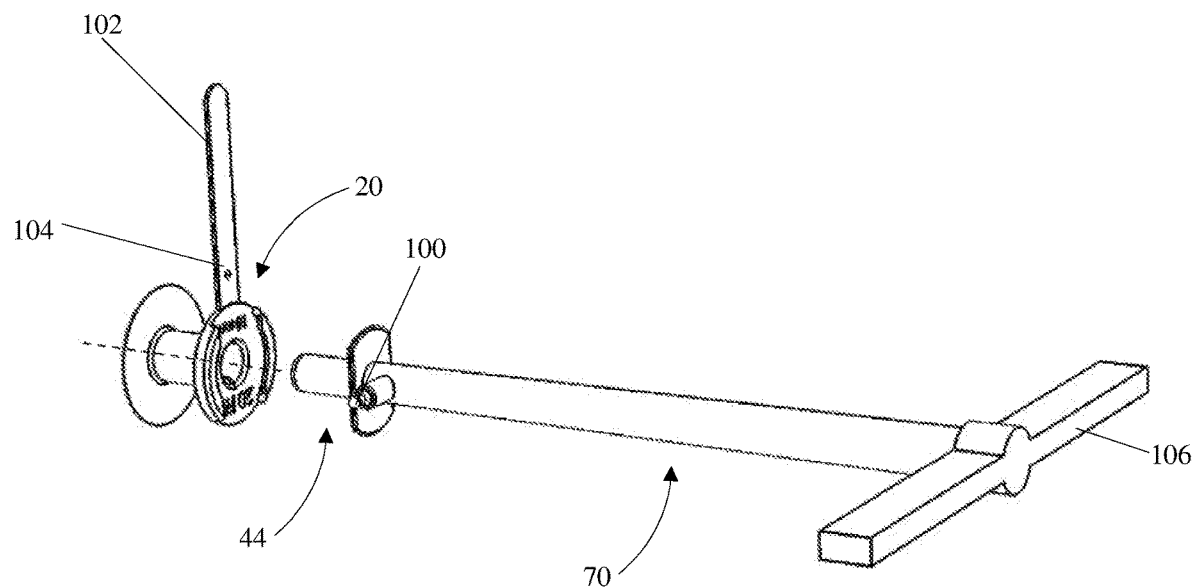
FIG. 22 is a perspective view of an insertion tool approaching a voice prosthesis unit, according to at least one embodiment of the present disclosure.
Figure 23:
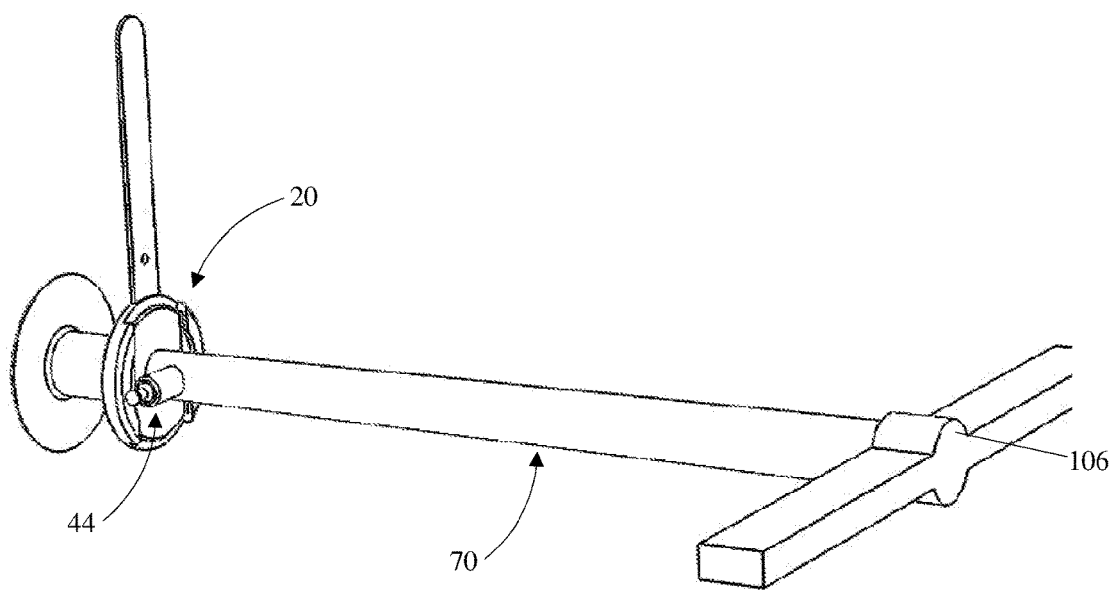
FIG. 23 is a perspective view of an insertion tool engaging a voice prosthesis unit, according to at least one embodiment of the present disclosure.

As in FIGS. 22-23, the insertion tool 68 can then be used to manipulate the inner cannula into the outer cannula. The inner cannula stem can be inserted into the passageway 34 of the outer cannula.

Figure 24:
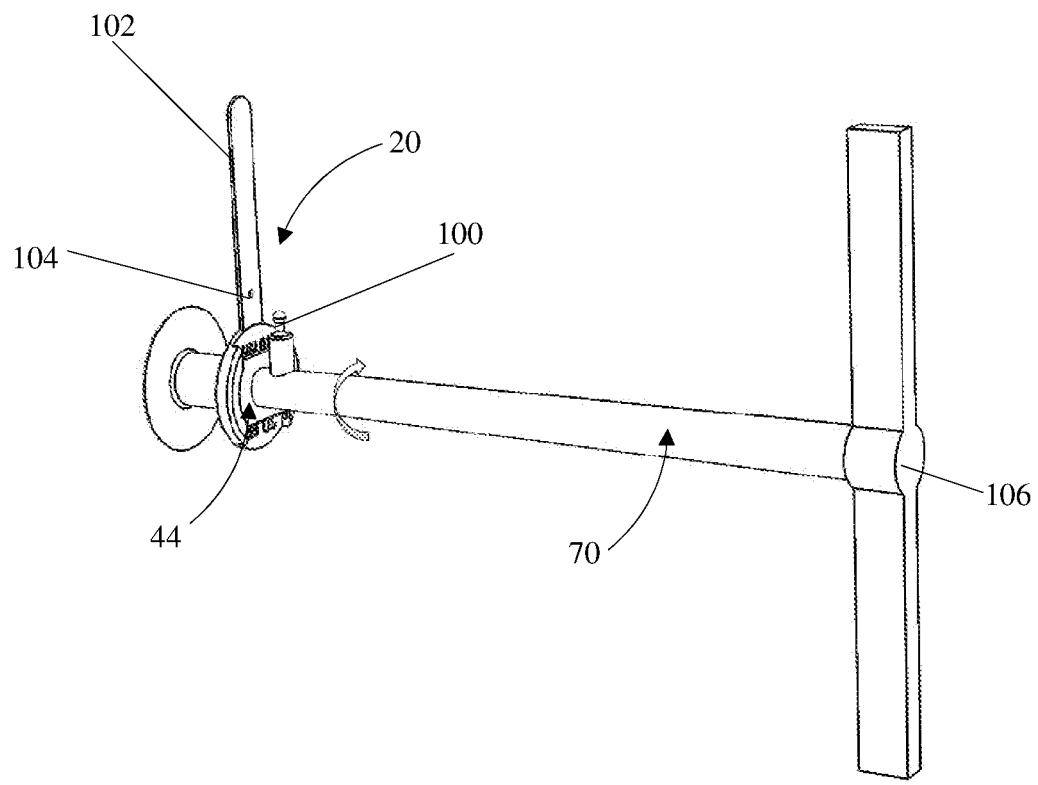
FIG. 24 is a perspective view of an insertion tool engaging a voice prosthesis unit with the insertion tool rotated 90 degrees, according to at least one embodiment of the present disclosure.

Now referring to FIG. 24, the insertion tool 68 is rotated 90 degrees. The T-handle 106 may aid in rotation. As the insertion tool 68 and inner cannula 44 are secured, the inner cannula 44 will rotate with the insertion tool 68. The proximal flange 52 of the inner cannula 44 will slide into the slots 40 of the outer cannula proximal flange 28. At this point the inner cannula and the outer cannula are secured. The nubs 36 of the outer cannula 20 will be extending into the windows of the inner cannula (not pictured).

Figure 25:
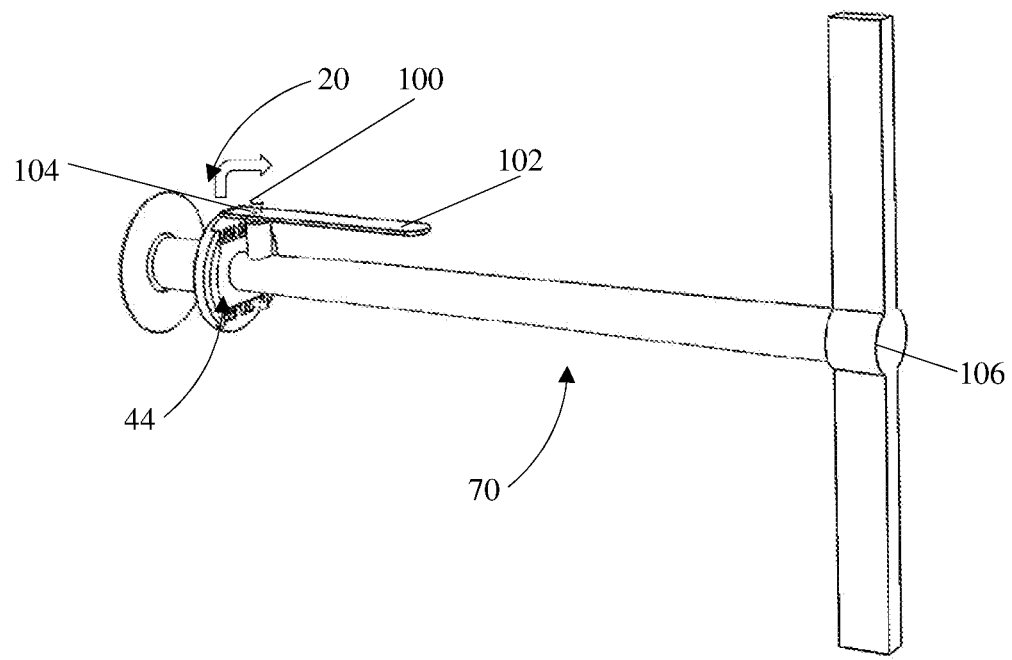
FIG. 25 is a perspective view of an insertion tool engaging a voice prosthesis unit with the insertion tool rotated 90 degrees whereby a portion of the voice prosthesis unit engages a portion of the insertion tool, according to at least one embodiment of the present disclosure.

As shown in FIG. 25. The outer cannula also comprises a tab 102 extending from the proximal flange 52. The tab 102 further comprises a hole 104. The outer cylinder of the insertion tool also comprises a peg 100 extending perpendicular from the outer cylinder. The tab 102 may be bent such that the hole 104 aligns onto the peg 100, further securing the devices.

The present disclosure includes disclosure of an affordable and easy to use disposable inner cannula that provides quick and convenient removal for cleaning or replacement. This offers a solution for patients who have the problem of requiring very frequent voice prosthesis replacements due to excessive candida growth and allows a greater degree of independence. The inner cannula can be changed by the laryngectomy on a regular basis, such as 1-2 weeks or other times as desired.

As referenced herein, the inner cannula fits inside the outer cannula. It has a lock to keep it from coming out, and it is easily removed for cleaning. The inner cannula can be removed, cleaned, and replaced allowing for the outer tube to remain in place. There are therefore no more worries about leaky valves or candida build up. Exemplary inner cannulas of the present disclosure will fit and work with different lengths of outer cannulas. Exemplary inner cannulas can be inserted and removed by patent or caregiver, and are easy and inexpensive to manufacture.

As noted herein, mechanical inserters (insertion tools 68) are designed to assist in the insertion and removal of the inner cannula into and out of the outer cannula. The insertion tool 68, in at least one embodiment, has a housing made of ridged plastic and a plunger rod that on one end has the locking wedge feature and on the other end a plunger feature for thumb actuation. In at least one embodiment, there is a spring in the housing that will bring back the plunger into its desired position after the thumb is released.

Insertion tools 68 of the present disclosure offer a safe and secure way to place the inner cannula 44 into the outer cannula 20 so that the patient and or caregiver can safely change the inner valve cannula 44, alleviating the need for a formal medical practitioner. Such devices and systems are simple and safe.

While various embodiments of devices for a voice prosthesis and methods for deploying and using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A voice prosthesis device, comprising:
   an outer cannula comprising a distal flange and a proximal flange connected by an annular first stem, the annular first stem defining a passageway therethrough;
   an inner cannula comprising a distal end and a proximal flange connected by an annular second stem, the annular second stem defining a passageway therethrough; and
   wherein the inner cannula comprises a valve;
   wherein the outer cannula comprises a slot configured to secure the proximal flange of the inner cannula;
   wherein the slot extends along a portion of the proximal flange of the outer cannula;
   wherein the proximal flange of the inner cannula has an obround shape; and
   wherein the proximal flange of the inner cannula has a thickness less than a thickness of the slot.

2. The voice prosthesis device of claim 1, further comprising:
   windows disposed on the annular second stem of the inner cannula at or near the proximal flange of the inner cannula, wherein the windows are configured to receive protrusions of an insertion tool, wherein the protrusions are configured to extend through the windows.

3. The voice prosthesis device of claim 1, wherein the annular first stem comprises retaining nubs on an inner surface of the annular first stem, and wherein the annular second stem comprises windows.

4. The voice prosthesis device of claim 3, wherein said windows and retaining nubs are aligned with one another.

5. A voice prosthesis device, comprising:
   an inner cannula comprising a distal end and a proximal flange connected by a annular second stem, the annular second stem defining a passageway therethrough; and
   an outer cannula comprising a distal flange and a proximal flange connected by an annular first stem, the annular first stem defining a passageway therethrough;
   wherein the proximal flange of the inner cannula has an obround shape, and wherein the outer cannula defines a slot configured to secure the proximal flange of the inner cannula.

6. The voice prosthesis device of claim 5, wherein the slot has a thickness, wherein the slot extends along a portion of the proximal flange of the outer cannula, and wherein the proximal flange of the inner cannula has a thickness less than the thickness of the slot.

7. The voice prosthesis device of claim 5, wherein the inner cannula comprises a valve.

8. The voice prosthesis device of claim 5, further comprising:
   windows disposed on the second annular stem at or near the proximal flange of the inner cannula.

9. The device of claim 8, comprising part of a system, the system further comprising:
   an insertion tool configured for at least partial insertion into the windows disposed on the second annular stem.

10. The device of claim 9, comprising part of the system, wherein the insertion tool comprises an inner cylinder slidably disposed within an outer cylinder.

11. The device of claim 10, comprising part of the system, wherein the outer cylinder comprises a distal end and apertures on the distal end, and wherein the inner cylinder comprises a distal end and protrusions that extend through the apertures.

12. The device of claim 11, comprising part of the system, wherein the inner cylinder has two separated ends at the distal end of the inner cylinder.

13. The device of claim 12, comprising part of the system, wherein the inner cylinder has a first position wherein in the first position the protrusions are retracted into the apertures.

14. The device of claim 13, comprising part of the system, wherein the inner cylinder has a second position wherein in the second position the protrusions are extending through the apertures.

15. The voice prosthesis device of claim 8, wherein the inner cannula comprises a valve.

16. The voice prosthesis device of claim 1, further comprising:
   windows disposed on the second annular stem at or near the proximal flange of the inner cannula.

17. The device of claim 16, comprising part of a system, the system further comprising:
   an insertion tool configured for at least partial insertion into the windows disposed on the second annular stem.

18. The device of claim 17, comprising part of the system, wherein the insertion tool comprises an inner cylinder slidably disposed within an outer cylinder.

19. The device of claim 18, comprising part of the system, wherein the outer cylinder comprises a distal end and apertures on the distal end, wherein the inner cylinder comprises a distal end and protrusions that extend through the apertures, and wherein the inner cylinder has two separated ends at the distal end of the inner cylinder.

20. The device of claim 19, comprising part of the system, wherein the inner cylinder has a first position wherein in the first position the protrusions are retracted into the apertures, and wherein the inner cylinder has a second position wherein in the second position the protrusions are extending through the apertures.

* * * * *